(12) United States Patent
Lewis et al.

(10) Patent No.: US 8,564,770 B1
(45) Date of Patent: Oct. 22, 2013

(54) SYSTEM FOR IN-SITU DETECTION OF PLANT EXPOSURE TO TRICHLOROETHYLENE (TCE)

(75) Inventors: Mark David Lewis, Long Beach, MS (US); Daniel J. Anderson, Carriere, MS (US); Lee A. Newman, Camillus, NY (US); Amy G. Keith, Madison, AL (US)

(73) Assignee: The United States of America as Represented by the Administrator of the National Aeronautics and Space Administration, Washington, DC (US)

(*) Notice: Subject to any disclaimer, the term of this patent is extended or adjusted under 35 U.S.C. 154(b) by 352 days.

(21) Appl. No.: 13/150,832

(22) Filed: Jun. 1, 2011

(51) Int. Cl.
*G01J 3/40* (2006.01)
*G01J 3/52* (2006.01)

(52) U.S. Cl.
USPC .......................................... 356/303; 356/421

(58) Field of Classification Search
USPC ........................................ 356/303, 402–425
See application file for complete search history.

(56) References Cited

U.S. PATENT DOCUMENTS

| | | | |
|---|---|---|---|
| 5,525,520 A | 6/1996 | Dinh | |
| 6,020,587 A | 2/2000 | Spiering et al. | |
| 6,052,187 A | 4/2000 | Krishnan et al. | |
| 6,683,970 B1* | 1/2004 | Satake et al. | 382/110 |
| 6,947,144 B2* | 9/2005 | Kim et al. | 356/417 |
| 7,003,405 B1* | 2/2006 | Ho | 702/32 |
| 7,112,806 B2 | 9/2006 | Lussier | |
| 7,408,145 B2 | 8/2008 | Holland | |
| 7,417,731 B1* | 8/2008 | Masten | 356/328 |
| 7,487,662 B2 | 2/2009 | Schabron et al. | |
| 2003/0040121 A1* | 2/2003 | Sivavec et al. | 436/126 |
| 2004/0130720 A1* | 7/2004 | Maeda et al. | 356/419 |
| 2005/0126428 A1* | 6/2005 | Lee et al. | 106/1.21 |
| 2007/0061098 A1 | 3/2007 | Delin et al. | |
| 2007/0090059 A1 | 4/2007 | Plummer et al. | |
| 2008/0239293 A1 | 10/2008 | Fuchigami et al. | |
| 2008/0291455 A1 | 11/2008 | Holland | |
| 2009/0056418 A1 | 3/2009 | Cole et al. | |
| 2010/0111369 A1* | 5/2010 | Lussier | 382/110 |

FOREIGN PATENT DOCUMENTS

| | | |
|---|---|---|
| CN | 1715880 A | 1/2006 |
| CN | 1945319 A | 4/2007 |

OTHER PUBLICATIONS

Phytoremediation of Organics Action Team, Evaluation of Phytoremediation for Management of chlorinated Solvents in Soil and Groundwater, The Remediation Technologies Development Forum (RTDF), Jan. 2005, EPA 542-R-05-001, USEPA, Cincinnati, OH.

Josep Penuelas et al., Leaf Reflectance and Photo and Antioxidant Protection in Field-Grown Summer-Stressed *Phillyrea angustifolia*. Optical Signals of Oxidative Stress?, New Phytologist, 2004, 115-124, 162, Spain.

* cited by examiner

*Primary Examiner* — Gregory J Toatley
*Assistant Examiner* — Shawn Decenzo
(74) *Attorney, Agent, or Firm* — Peter J. Van Bergen; James J. McGroary

(57) ABSTRACT

A system detects a plant's exposure to trichloroethylene (TCE) through plant leaf imaging. White light impinging upon a plant's leaf interacts therewith to produce interacted light. A detector is positioned to detect at least one spectral band of the interacted light. A processor coupled to the detector performs comparisons between photonic energy of the interacted light at the one or more spectral bands thereof and reference data defining spectral responses indicative of leaf exposure to TCE. An output device coupled to the processor provides indications of the comparisons.

19 Claims, 1 Drawing Sheet

SYSTEM FOR IN-SITU DETECTION OF PLANT EXPOSURE TO TRICHLOROETHYLENE (TCE)

ORIGIN OF THE INVENTION

The invention described herein was made in the performance of work under a NASA contract and by an employee of the United States Government and is subject to the provisions of Public Law 96-517 (35 U.S.C §202) and may be manufactured and used by or for the Government for governmental purposes without the payment of any royalties thereon or therefor. In accordance with 35 U.S.C §202, the contractor elected not to retain title.

BACKGROUND OF THE INVENTION

1. Field of the Invention

This invention relates to the detection of the presence of trichloroethylene (TCE) in soil or groundwater. More specifically, the invention is an in-situ system that can non-invasively detect if a plant has been exposed to TCE as an indication that TCE is present in the soil or groundwater.

2. Description of the Related Art

Trichloroethylene (TCE) is a chlorinated hydrocarbon which has been used in a variety of applications, most widely as an industrial solvent. However, TCE's toxicity to human and animal populations has been well documented. Accordingly, TCE has been banned in the food and pharmaceutical industries since the 1970s. Still, TCE is listed as one of the most prevalent groundwater contaminants in the United States, and is found at over 60% of the Environmental Protection Agency's National Priorities List (NPL) cites. Additionally, TCE's use in dry cleaning and as an industrial solvent indicates that there might be hundreds of small sites around the country where TCE has migrated into the soil and/or groundwater.

Currently, the main problems associated with detecting TCE in soil or groundwater is the time and cost involved. The traditional detection method involves going into the field and drilling monitoring wells, sampling the water over time, analyzing the data, collecting and analyzing samples again, analyzing groundwater flow patterns, and making a 'best guess' as to where the contaminant is located and how far it has moved. The costs associated with this process are significant as the cost associated with just the lab processing of each water sample is roughly $250.

Another approach to detecting TCE in groundwater is to check for the presence of TCE or trichloroacetic acid (TCAA) in plants. That is, it is well known in the phytoremediation field that plants take up TCE and metabolize it to form TCAA. More specifically, groundwater is taken up by plants and is a reactant in the photosynthesis process. If TCE is present in groundwater, evidence shows that the TCE is taken up by plants when absorbing groundwater. Plants then metabolize the TCE into multiple metabolites, with TCAA being the most prevalent in a plant's leaves.

While laboratory methods exist for the analysis of TCE in a plant's trunk, stems and leaves, these analysis methods are labor intensive, can be expensive, and/or can damage a plant. For example, tree cores have been used in some TCE detection methods. However, the act of taking a core from a tree risks introducing a fugal infection into the tree and also requires of use of special laboratory instrumentation. Since TCAA is more stable than TCE and can be sampled in a plant's leaves, some analysis methods have focused on a plant's leaves in order to avoid the drawbacks associated with using tree cores. However, the leaves have to be harvested, packed on ice, shipped to an analytical lab, and require a two day procedure to derivatize the TCAA so that it can be analyzed by gas chromatography. Further, even if a particular leaf has measurable levels of TCAA, this is not a dispositive indicator since each leaf from a plant can have different TCAA levels due to a variety of factors.

SUMMARY OF THE INVENTION

Accordingly, it is an object of the present invention to provide a system for detecting a plant's exposure to TCE.

Another object of the present invention is to provide a system for in-situ and non-invasive detection of a plant's exposure to TCE.

Other objects and advantages of the present invention will become more obvious hereinafter in the specification and drawings.

In accordance with the present invention, a system is provided for detecting a plant's exposure to TCE by imaging the plant's leaves. A source causes white light to impinge upon a plant's leaf for interaction therewith where the interaction produces interacted light. A light detector is positioned to detect at least one spectral band of the interacted light. In general, each such spectral band is from the 400-1000 nanometer spectra of wavelengths. A processor coupled to the light detector performs comparisons between photonic energy of the interacted light at the one or more spectral bands thereof and reference data defining spectral responses indicative of leaf exposure to TCE. An output device coupled to the processor provides indications of the comparisons.

BRIEF DESCRIPTION OF THE DRAWING(S)

Other objects, features and advantages of the present invention will become apparent upon reference to the following description of the preferred embodiments and to the drawings, wherein corresponding reference characters indicate corresponding parts throughout the several views of the drawings and wherein.

DESCRIPTION OF THE PREFERRED EMBODIMENT(S)

Figure 1:
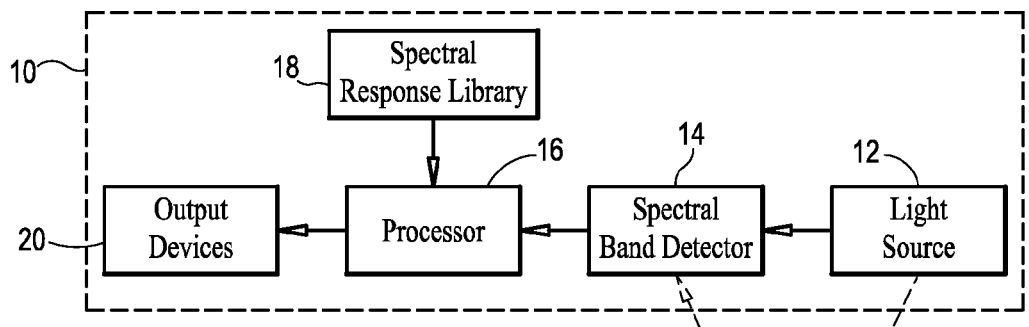
FIG. 1 is a schematic view of a system for in-situ imaging of the leaf of a plant in accordance with an embodiment of the present invention.

Referring now to the drawings and more particularly to FIG. 1, a system for in-situ TCE exposure detection is shown and is referenced by the elements contained within dashed line box 10 that can also be indicative of a housing (e.g., a hand-held housing) to support the elements of system 10. The particular shape, size, construction, etc., of such a housing is not a limitation of the present invention. System 10 is configured to detect TCE exposure in a plant's leaf 100, while allowing leaf 100 to remain attached to a stem 102 of the plant. That is, system 10 is non-invasive and non-destructive with respect to leaf 100 and the plant to which it is attached.

System 10 includes a light source 12, a spectral band detector 14, a processor 16 that can be programmed or supplied with a library of spectral responses 18, and one or more output devices 20. In the illustrated embodiment, light source 12 and spectral band detector 14 are on the same side of leaf 100. However, the present invention is not so limited as light source 12 and spectral band detector 14 could be disposed on opposing sides of leaf 100 as will be explained further below.

Light source 12 is a source of white light. Accordingly, light source 12 can be naturally occurring (e.g., sunlight) or could be provided by a man-made source (e.g., incandescent light source, light emitting diode (LED), etc.) without departing from the scope of the present invention. In either case, the light from light source 12 (referenced by dashed line 12A) illuminates or impinges on a surface of leaf 100. After interacting with leaf 100, a portion of the interacted light is reflected from leaf 100 as referenced by dashed line 12B.

Spectral band detector 14 is positioned in system 10 to detect interacted light 12B. In the present invention, detector 14 collects light spectra from about the 400 nanometer to 1000 nanometer wavelengths. More specifically, detector 14 can be configured to be sensitive to one or more spectral bands from the 400-1000 nanometer spectra. For example, in various tests of the present invention made on mimosa trees, pin cherry trees, arundo grass, Judas trees, waxmyrtle plants, poplar trees, sumac shrubs/trees, and willow trees, spectral bands centered on 527 nanometers (i.e., the green spectral band), 627 nanometers (i.e., the red spectral band), and 745, 883 and 895 nanometers (i.e., near-infrared spectral band), have provided distinguishable responses between leaves of plants that have been exposed to TCE and those that have not be so-exposed. However, it is to be understood that system 10 is not limited to operation in these spectral bands as others may provide equal or better results depending on, for example, the type of plant/leaves being examined/analyzed.

Figure 2:
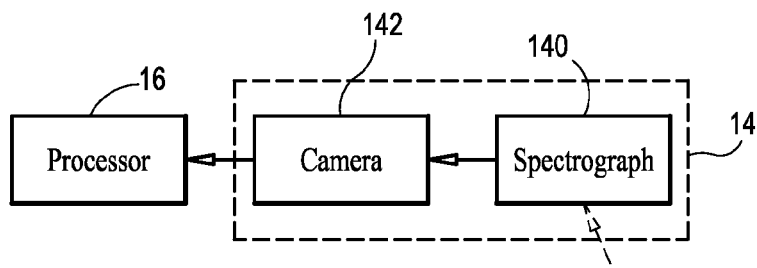
FIG. 2 is a schematic view of a spectral band detector in accordance with an embodiment of the present invention.

An exemplary embodiment of spectral band detector 14 is shown schematically in FIG. 2. A spectograph 140 is used to filter or separate interacted light 12B into specific spectral bands of interest. A camera 142 (e.g., an array of light sensors) is used to capture light in the spectral bands of interest. That is, camera 142 measures the photonic energy of the light in the spectral bands of interest and provides such photonic energy information to processor 16.

Processor 16 is any device or system that can be used to process the photonic energy supplied by detector 14. In general, processor 16 performs comparisons between the photonic energy of interacted light 12B in the spectral bands of interest and reference data in spectral response library 18 that defines photonic energy levels for TCE-exposed plant leaves versus non-exposed plant leaves. For example, library 18 could be divided into groups of reference data with each such group being associated with a different plant species. The reference data for each group could include data taken by system 10 from TCE-exposed plant leaves and data taken by system 10 from non-exposed plant leaves for a particular species. The data could simply be raw lab sample data or calibrated sample data without departing from the scope of the present invention. Data provided by spectral response library 18 could be stored by processor 16, could be stored in a peripheral storage device coupled to processor 16, or could be supplied to processor 16 as needed. Methods for generating the data in spectral response library 18 can be accomplished in a variety of ways (e.g., in a laboratory) without departing from the scope of the present invention.

Processor 16 provides the results of the above-described comparisons to one or more output devices 20. For example, a visual display could be used to present numeric and/or graphic presentations of the results. Additionally or alternatively, an audible device could be used to produce different audible tones depending on the results of the comparisons.

Figure 3:
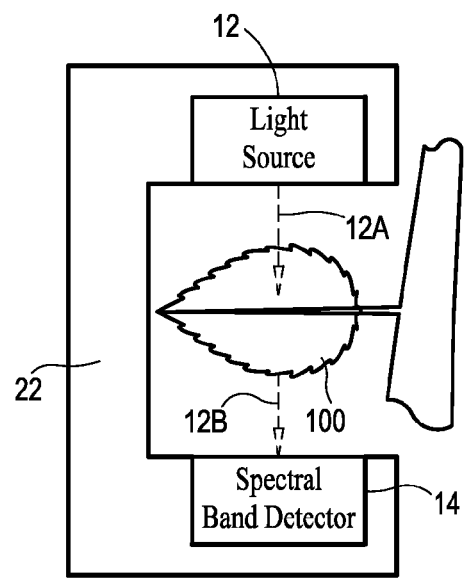
FIG. 3 is a schematic view of a housing used to support a light source and spectral band detector on opposing sides of the leaf of a plant in accordance with another embodiment of the present invention.

As mentioned above, the present invention is not limited to the detection of interacted light 12B that has been reflected from leaf 100. Accordingly, FIG. 3 depicts another embodiment of the present invention where a housing 22 supports and positions light source 12 and detector 14 on opposing sides of leaf 100. Note that the remaining elements of the present invention's system are not illustrated in FIG. 3. In this embodiment, impinging light 12A also causes the production of interacted light 12C that has passed through leaf 100 and the side of leaf 100 that opposes the side thereof illuminated by impinging light 12A.

The advantages of the present invention are numerous. The system provides in-situ TCE-exposure detection in plant leaves as an indicator of the presence of TCE in a soil or groundwater environment. The system is non-invasive and will not harm plant life. The system provides a readily-implemented and cost-effective solution to the testing and monitoring of groundwater environments and, therefore, will aid in the reduction of costs associated with the clean up of polluted land and water.

Although the invention has been described relative to a specific embodiment thereof, there are numerous variations and modifications that will be readily apparent to those skilled in the art in light of the above teachings. For example, the system of the present invention could be adapted to examine plant leaves for exposure to other types of soil, groundwater or even airborne contaminants that are absorbed by a plant. It is therefore to be understood that, within the scope of the appended claims, the invention may be practiced other than as specifically described.

What is claimed as new and desired to be secured by Letters Patent of the United States is:

1. A system for detecting a plant's exposure to trichloroethylene (TCE), comprising:
    a source of white light wherein said white light is adapted to impinge upon a plant's leaf for interaction therewith, and wherein said interaction produces interacted light;
    a light detector positioned to detect at least one spectral band of said interacted light, wherein said at least one spectral band is from the 400-1000 nanometer spectra of wavelengths;
    a processor coupled to said light detector for performing comparisons between photonic energy of said interacted light at said at least one spectral band thereof and reference data defining spectral responses indicative of plant exposure to TCE; and
    an output device coupled to said processor for providing indications of said comparisons.

2. A system as in claim 1, further comprising a housing supporting said source of white light and said light detector, said housing adapted to position said source of white light and said light detector on one side of the plant's leaf.

3. A system as in claim 1, further comprising a housing supporting said source of white light and said light detector, said housing adapted to position said source of white light and said light detector on opposing sides of the plant's leaf.

4. A system as in claim 1, further comprising a hand-held housing supporting said source of white light and said light detector.

5. A system as in claim 1, wherein said source of white light is a naturally occurring source.

6. A system as in claim 1, wherein said source of white light is a man-made source.

7. A system as in claim 1, wherein said output device provides at least one of a visual output and an audio output.

8. A system as in claim 1, wherein said light detector includes:

a spectrograph for separating said interacted light into said at least one spectral band thereof; and a camera coupled to said spectrograph for measuring said photonic energy of said interacted light at each said at least one spectral band thereof.

9. A system for detecting plant exposure to trichloroethylene (TCE), comprising:

a source of white light wherein said white light is adapted to impinge upon a plant's leaf for interaction therewith, and wherein said interaction produces interacted light;

a light detector positioned to detect at least one spectral band of said interacted light, wherein said at least one spectral band is from the 400-1000 nanometer spectra of wavelengths;

a hand-held housing supporting said source of white light and said light detector, said hand-held housing adapted to position said source of white light and said light detector on one side of the plant's leaf;

a processor coupled to said light detector for performing comparisons between photonic energy of said interacted light at said at least one spectral band thereof and reference data defining spectral responses indicative of plant exposure to TCE; and an output device coupled to said processor for providing indications of said comparisons.

10. A system as in claim 9, wherein said source of white light is a naturally occurring source.

11. A system as in claim 9, wherein said source of white light is a man-made source.

12. A system as in claim 9, wherein said output device provides at least one of a visual output and an audio output.

13. A system as in claim 9, wherein said light detector includes:

a spectrograph for separating said interacted light into said at least one spectral band thereof; and a camera coupled to said spectrograph for measuring said photonic energy of said interacted light at each said at least one spectral band thereof.

14. A system for detecting the presence of trichloroethylene (TCE) in plant leaves, comprising:

a source of white light wherein said white light is adapted to impinge upon a plant's leaf for interaction therewith, and wherein said interaction produces interacted light;

a spectrograph for separating said interacted light into said at least one spectral band thereof, wherein said at least one spectral band is from the 400-1000 nanometer spectra of wavelengths;

a camera coupled to said spectrograph for measuring photonic energy of said interacted light at each said at least one spectral band thereof;

a processor coupled to said camera for performing comparisons between photonic energy of said interacted light at said at least one spectral band thereof and reference data defining spectral responses indicative of plant exposure to TCE; and an output device coupled to said processor for providing at least one of visual indications and audible indications of said comparisons.

15. A system as in claim 14, further comprising a housing supporting said source of white light and said light detector, said housing adapted to position said source of white light and said light detector on one side of the plant's leaf.

16. A system as in claim 14, further comprising a housing supporting said source of white light and said light detector, said housing adapted to position said source of white light and said light detector on opposing sides of the plant's leaf.

17. A system as in claim 14, further comprising a hand-held housing supporting said source of white light and said light detector.

18. A system as in claim 14, wherein said source of white light is a naturally occurring source.

19. A system as in claim 14, wherein said source of white light is a man-made source.

* * * * *